United States Patent
Guimont et al.

(10) Patent No.: US 10,835,465 B2
(45) Date of Patent: Nov. 17, 2020

(54) COMPOSITIONS FOR REMOVING NAIL POLISH

(71) Applicant: L'OREAL, Paris (FR)

(72) Inventors: Aline Aude Guimont, Westfield, NJ (US); Chunhua Li, Hillsborough, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/117,624

(22) Filed: Aug. 30, 2018

(65) Prior Publication Data

US 2019/0159990 A1    May 30, 2019

Related U.S. Application Data

(60) Provisional application No. 62/592,893, filed on Nov. 30, 2017.

(51) Int. Cl.
| | |
|---|---|
| *A61K 8/34* | (2006.01) |
| *A61Q 3/04* | (2006.01) |
| *A61K 8/37* | (2006.01) |
| *A61K 8/49* | (2006.01) |
| *A61K 8/60* | (2006.01) |
| *A61K 8/81* | (2006.01) |

(52) U.S. Cl.
CPC ............... *A61K 8/34* (2013.01); *A61K 8/345* (2013.01); *A61K 8/37* (2013.01); *A61K 8/4973* (2013.01); *A61K 8/60* (2013.01); *A61K 8/8152* (2013.01); *A61Q 3/04* (2013.01); *A61K 2800/28* (2013.01); *A61K 2800/30* (2013.01); *A61K 2800/31* (2013.01); *A61K 2800/48* (2013.01)

(58) Field of Classification Search
None
See application file for complete search history.

(56) References Cited

U.S. PATENT DOCUMENTS 9,987,212 B2    6/2018 MacNeill

FOREIGN PATENT DOCUMENTS

| CN | 101953769 A | 1/2011 |
| CN | 105078801 A | 11/2015 |
| JP | 2014139142 A | * 7/2014 |
| JP | 2014139142 A2 | 7/2014 |
| TW | 201210624 A | 3/2012 |

OTHER PUBLICATIONS

Gentle Nail Remover, Mintel GNPD, p. 1-2, Published on Aug. 2012.
Tommy Girl Sugar Scrub, Mintel GNPD, p. 1-2, Published on Nov. 2001.

* cited by examiner

*Primary Examiner* — Nannette Holloman
(74) *Attorney, Agent, or Firm* — Michael Tyerech; Runziti Zhao

(57) ABSTRACT

The invention relates to compositions for removing nail polish comprising a C2-C3 monoalcohol, glycerin, and propylene carbonate, wherein the glycerin and propylene carbonate are present in a glycerin to propylene carbonate ratio by weight of at least 1:3 and the concentration by weight of ethanol is at least about 16%. Methods of removing nail polish and moisturizing the hands are also provided.

18 Claims, 1 Drawing Sheet

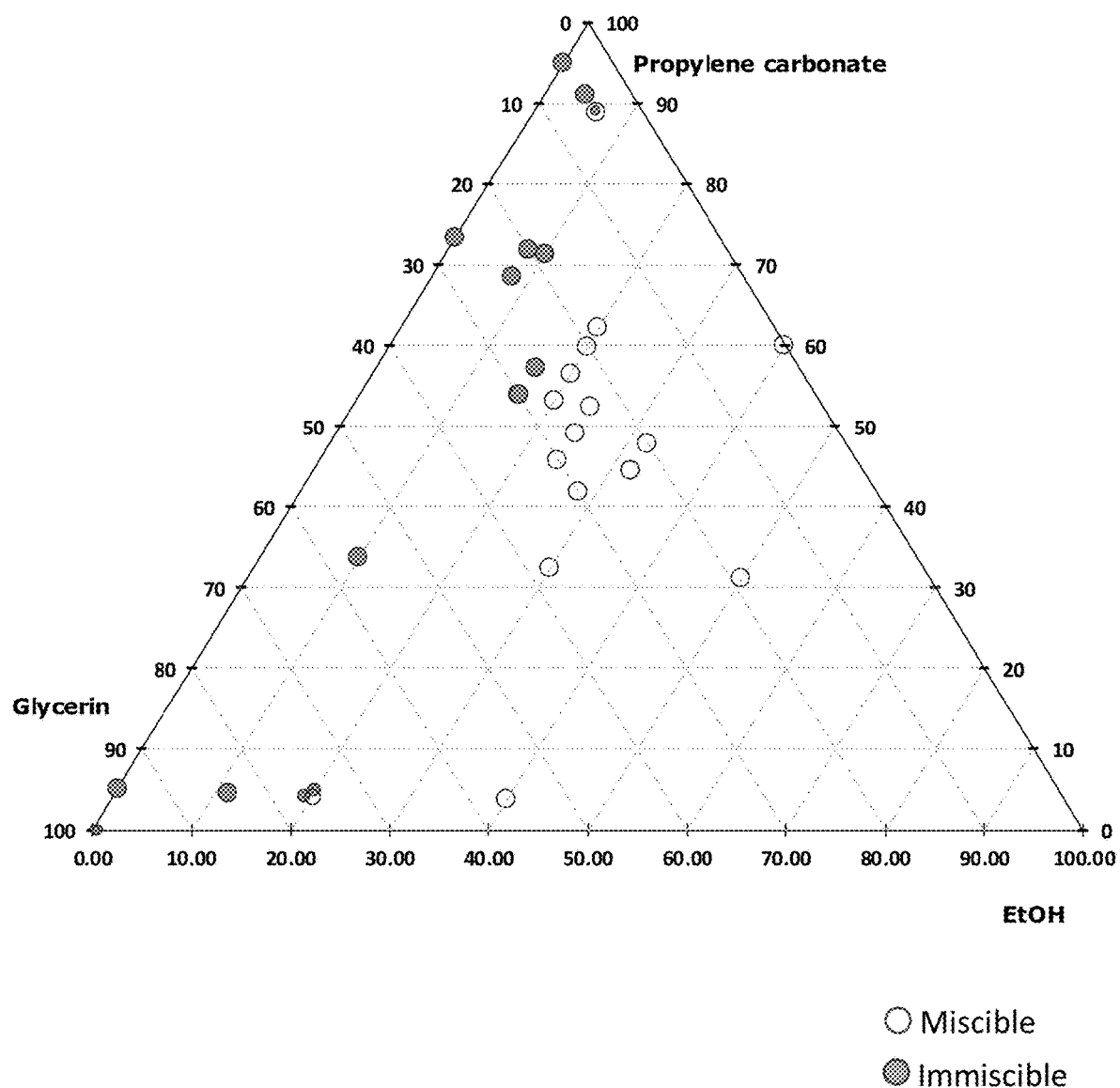

COMPOSITIONS FOR REMOVING NAIL POLISH

CROSS-REFERENCE TO RELATED APPLICATION

This application claims the benefit of U.S. Provisional Application No. 62/592,893, filed Nov. 30, 2017.

FIELD OF THE INVENTION

The present invention relates to compositions and methods for removing nail polish.

Discussion of the Background

Nail polish compositions are typically designed to provide long-lasting color to nails. Because of the materials used in nail polish compositions to obtain the desired properties, it has proven difficult to remove such nail polish compositions from nails without adversely affecting the nails and/or staining cuticles of the nails.

In particular, the inventors have recognized the need to provide efficacious nail polish removal using compositions that are free of harsh solvents such as acetone.

SUMMARY OF THE INVENTION

The present invention relates to compositions for removing nail polish comprising a C2-C3 monoalcohol, glycerin, and propylene carbonate. The glycerin and propylene carbonate are present in a glycerin to propylene carbonate ratio by weight of at least 1:3. The concentration by weight of C2-C3 monoalcohol is at least about 16%.

The present invention also relates to methods for removing nail polish from nails and moisturizing the hands of a subject. The method includes applying a composition to the hands and to nails of a subject onto which the nail polish had been previously applied and removing the nail polish from the nails. The composition includes a C2-C3 monoalcohol, glycerin, and propylene carbonate. The glycerin and propylene carbonate are present in a glycerin to propylene carbonate ratio by weight of at least 1:3. The concentration by weight of C2-C3 monoalcohol is at least about 16%.

It is to be understood that both the foregoing general description and the following detailed description are exemplary and explanatory only, and are not restrictive of the invention.

BRIEF DESCRIPTION OF FIGURES

FIG. 1 is a phase diagram using data developed by the inventors, showing relative concentrations of glycerin, propylene carbonate and ethanol and a region of miscibility.

DETAILED DESCRIPTION OF THE INVENTION

As used herein, the expression "at least one" means one or more and thus includes individual components as well as mixtures/combinations. All percentages listed are by weight unless otherwise noted.

Other than in the operating examples, or where otherwise indicated, all numbers expressing quantities of ingredients and/or reaction conditions are to be understood as being modified in all instances by the term "about," meaning within 10% to 15% of the indicated number.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful.

For purposes of the compositions and methods of the present invention where the invention "consists essentially of" the identified ingredients and/or process steps, the two "basic and novel properties" of such compositions and/or methods are "removing nail polish from nails," "phase stability," and "minimizing staining of cuticles."

Compositions for Removing Nail Polish

In accordance with the present invention, compositions for removing nail polish comprising a C2-C3 monoalcohol, glycerin, and propylene carbonate are provided. The glycerin and propylene carbonate are present in a glycerin to propylene carbonate ratio by weight of at least 1:3. The concentration by weight of C2-C3 monoalcohol is at least about 16%.

Glycerin

In accordance with the present invention, compositions for removing nail polish comprising glycerin (a.k.a., glycerol, glycerine, propanetriol, 1,2,3-Trihydroxypropane or 1,2,3-Propanetriol) are provided. By glycerol, it is meant the polyol compound $C_3H_8O_3$, having the general structure below as well as, in certain embodiments, isomers thereof.

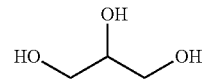

The inventors have found that glycerin contributes to the ability of compositions of the present invention to resist staining of the cuticles from nail polish that is removed from the nails. Accordingly, glycerin may be present in the compositions of the present invention in an amount of at least about 10% by weight, such as at least about 15% by weight, such as at least about 20% by weight. In certain embodiments the glycerin is present in a concentration that is less than 50% by weight. For example, the glycerin may be present in concentration ranges from about 5% to about 50%, from about 10% to about 50%, from about 15% to about 50%, from about 20% to about 50%, from about 10% to about 40%, from about 15% to about 30%, with all weights being based on the weight of the composition.

C2-C3 Monoalcohol

In accordance with the present invention, compositions for removing nail polish comprising a C2-C3 monoalcohol are provided.

"C2-C3 monoalcohol" means an alcohol having 2 or 3 carbon atoms such as ethanol, propanol, and isopropanol. In certain embodiments the C2-C3 monoalcohol is ethanol.

The C2-C3 monoalcohol is present in the compositions of the present invention in an amount greater than 16% by weight. In certain embodiments, the C2-C3 monoalcohol is present in a concentration of at least about 20%. In certain other embodiments the concentration of C2-C3 monoalcohol is present in a concentration of from about 16% to about 40%, such as from about 20% to about 35%, such as from about 20% to about 30%.

Propylene Carbonate

In accordance with the present invention, compositions for removing nail polish comprising propylene carbonate are provided. Propylene carbonate is a carbonate ester derived from propylene glycol and has a chemical formula of $CH_3C_2H_3O_2CO$.

The propylene carbonate may be present in the compositions of the present invention in an amount greater than 10% by weight, such as greater than 15% by weight, such as greater than 20% by weight, such as less than 50% by weight, including all ranges and subranges therebetween such as, for example, from 10% to 63%, from 15% to 50%, from 20% to 50%, from 10% to 40%, from 15% to 30%, etc., with all weights being based on the weight of the composition.

The inventors have recognized that sufficiently high levels of glycerin and/or sufficiently high ratios of glycerin to propylene carbonate are needed for formulations that have reduced staining of the cuticles upon removal nail polish. Accordingly, compositions of the present invention have ratios of glycerin to propylene carbonate that are at least about 1:3. In other words the glycerin and propylene carbonate are present in a glycerin to propylene carbonate ratio by weight of at least 1:3. In certain other embodiments of the invention compositions of the present invention have ratios of glycerin to propylene carbonate that are at least about 1:2.2, such as at least about 1:1.5. For sake of clarity, by "ratios of glycerin to propylene carbonate that are at least about 1:3," for example, it is meant that if the concentration by weight of propylene carbonate is 15%, then the concentration by weight of glycerin is 5% by weight or higher.

In certain embodiments of the invention, the composition is predominantly comprised of the C2-C3 monoalcohol, glycerin, and propylene carbonate. In certain embodiments the C2-C3 monoalcohol, glycerin, and propylene carbonate collectively comprise at least about 75% of the composition.

In compositions of the present invention, the C2-C3 monoalcohol, glycerin, and propylene carbonate generally are believed to exist as components of a multicomponent solution phase. In other words, the C2-C3 monoalcohol, glycerin, and propylene carbonate are present in concentrations such that these components are jointly co-soluble in one another.

In certain embodiments, the multicomponent solution phase consists of or consists essentially of the C2-C3 monoalcohol, glycerin, and propylene carbonate. In other embodiments, the multicomponent solution phase includes one more additional components. The one more additional components may, in certain embodiments comprise no more than about 10% by weight of the multicomponent solution phase. The nature of the one or more additional components may vary, but are generally selected from ingredients that are capable of dissolving in a single phase mixture of the C2-C3 monoalcohol, glycerin, and propylene carbonate. Examples of suitable additional components include fragrances, preservatives, polymeric thickening agents, polar oils, polar waxes, polymeric suspending agents, surfactants, emulsifiers, and the like.

Polymeric Thickening Agent

In accordance with the present invention, compositions for removing nail polish comprising at least one thickening agent are provided. Non-limiting examples of thickening agents that may be used according to various embodiments of the present invention include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be used.

According to certain embodiments, the thickening agent is an acrylic thickening agent (acrylic thickener) or an acrylamide thickening agent (acrylamide thickener).

"Acrylic thickening agent" or "acrylic thickener" as used herein refers to polymers based upon one or more (meth) acrylic acid (and corresponding (meth)acrylate) monomers or similar monomers.

"Acrylamide thickening agent" or "acrylamide thickener" as used herein refers to polymers based upon one or more acrylamide monomers or similar monomers.

According to certain embodiments, the thickening agent comprises at least one monomer performing a weak acid function such as, for example, acrylic acid, methacrylic acid, itaconic acid, crotonic acid, maleic acid and/or fumaric acid.

According to certain embodiments, the thickening agent comprises at least one monomer performing a strong acid function such as, for example, monomers having a function of the sulfonic acid type or phosphonic acid type, such as 2-acrylamido-2-methylpropane sulfonic acid (AMPS).

According to certain embodiments, the thickening agent may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vi nyloxyethacrylate or methacrylate, formaldehyde, glyoxal, and compositions of the glycidylether type such as ethyleneglycol diglycidylether, or epoxides.

Suitable acrylic thickeners are disclosed in U.S. patent application publication nos. 2004/0028637 and 2008/0196174, the entire contents of both of which are incorporated herein by reference.

Specific non-limiting examples of suitable thickening agents include homopolymers or copolymers of acrylic or methacrylic acids or the salts thereof and the esters thereof, such as the products sold under the names VERSICOL F or VERSICOL K by Allied Colloid, ULTRAHOLD 8 by Ciba-Geigy, polyacrylates and polymethacrylates such as the products sold under the names LUBRAJEL and NORGEL by Guardian, or under the name HISPAJEL by Hispano Chimica, polyacrylic acids of SYNTHALEN K type, polyacrylamides, copolymers of acrylic acid and of acrylamide sold in the form of the sodium salt thereof, such as under the names RETEN by Hercules, the sodium polymethacrylate such as sold under the name DARVAN 7 by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (INCI name: ammonium polyacryldimethyltauramide), crosslinked anionic copolymers of acrylamide and of AMPS, e.g. in the form of a water-in-oil emulsion, such as those sold under the name SEPIGEL 305 (INCI name: Polyacrylamide/C13-14 lsoparaffin/Laureth-7) and under the name SIMULGEL 600 (CTFA name: Acrylamide/Sodium acryloyldimethyltaurate copolymer/Isohexa-decane/Polysorbate 80) by SEPPIC, polyacrylic acid/alkyl acrylate copolymers of PEMULEN type, sodium acrylate/sodium acryloyldimethyl taurate such as that sold under the INCI name Sodium Acrylate/Sodium Acryloyldimethyl Taurate Copolymer & Hydrogenated Polydecene & Sorbitan Laurate & Trideceth-6 which is marketed by Lonza, Allendale, N.J., USA under the tradename ViscUpEZ. In certain embodiments, the thickening agent is selected from an acrylamide and a water soluble cellulose polymer (such as hydroxypropylmethylcellulose, ethylcellulose, and/or hydroxypropylcellulose), and combinations thereof.

According to certain embodiments, the thickening agent is a cellulose-based thickener. Suitable cellulose-based compounds include, but are not limited to, cellulose polymers, such as, for example, hydroxyethylcellulose, hydroxypropylcellulose, methylcellulose, and ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g., KLUCEL MF—both available from Ashland of Covington, Ky.

According to certain embodiments, the thickening agent is a polysaccharide. In general, polysaccharides may be divided into several categories. Polysaccharides that are suitable for use in the invention may be homopolysaccharides such as fructans, glucans, galactans and mannans or heteropolysaccharides such as hemicellulose. Suitable polysaccharides may be linear polysaccharides such as pullulan or branched polysaccharides such as gum arabic and amylopectin, or mixed polysaccharides such as starch.

The at least one thickening agent may be present in the compositions of the present invention in an amount greater than 0.05% by weight, such as greater than 0.1% by weight, such as greater than 0.5% by weight, such as greater than 1% by weight and may be less than 15% by weight, including all ranges and subranges therebetween such as, for example, from 0.1% to 15%, such as from 0.1% to 10%, such as from 0.5% to 10%, such as from 0.75% to 7.5%, such as from 1% to 5%, etc., with all weights being based on the weight of the composition.

The composition may comprise multiple phases. For example, the composition may comprise a multicomponent solution phase and a suspended solid phase that is suspended in the multicomponent solution phase. The suspended solid phase may include any of various ingredients that do not dissolve in the multicomponent solution phase and are capable of being suspended therein. According to certain notable embodiments, the suspended solid phase includes one or more abrasive compounds.

Abrasive Compound

In accordance with the present invention, compositions for removing nail polish comprising at least one abrasive compound (abrasive system) are provided. A "abrasive compound" is a compound capable of providing abrasion or mechanical exfoliation and in accordance with the present invention has one or more of the following characteristics:

(1) Surface roughness: particles with irregular edges provide for abrasion; (2) shape: the particles of the abrasive compound may have a non-angular shape such as a disc, oval or sphere; (3) average particle size: in the context of abrasive compounds from mineral origins, shells, seeds micronized fruit kernel powders, and the like. The particles of the abrasive may have a particle size of 1000 microns ($\mu$m) or less, such as 500 $\mu$m or less, such as 300 $\mu$m or less, such as 150 $\mu$m or less, such as 75 $\mu$m or less, such as, 50 $\mu$m or less such as 30 $\mu$m or less; and (4) hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrubeads), as well as synthetic polymeric materials such as polyethylene, polypropylene, polyethylene terephthalate, polymethlyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

The suspended solid phase may include other particulate material such as pigments, optical modifiers, tactile modifiers, and the like.

According to other embodiments, compositions of the present invention may also include an inorganic thickening agent. This may be an organoclay (hydrophobically treated clay), a hydrophilic clay, or other inorganic thicknener.

The term "hydrophilic clay" means a clay that is capable of swelling in water; this clay is activated in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin. Hydrophilic clays that may be mentioned include smectite products such as saponites, hectorites, montmorillonites, bentonites and beidellite. The term "lipophilic clay" (hydrophobically treated clay) means a clay that is capable of swelling in a lipophilic medium; this clay swells in activated in a hydrophobic solvent and thus forms a colloidal dispersion. Examples of lipophilic clays that may be mentioned include modified clays such as modified hectorite (Bentone Gel VCG from Elementis), and hectorites modified with a $C_{10}$ to $C_{22}$ fatty-acid ammonium chloride. Examples include hectorite modified with distearyldimethylammonium chloride (INCI name: disteardimonium hectorite).

In particular, among the thickening agents that may be used, mention may be made of silica particles. Suitable silicas include, but are not limited to, hydrophobic synthetic amorphous silicas, pyrogenic or fumed silica optionally with hydrophobic surface treatment with particle size less than 10 microns, such as less than 500 nm, such as less than 100 nm, such as from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained.

According to certain embodiments of the present invention, the compositions for removing nail polish are "essentially free" of acetone, water or both, "substantially free" of acetone, water, or both, or "free" of acetone, water or both. "Essentially free" means that the composition contains less than about 3% of the identified ingredient. "Substantially free" means that the composition contains less than about 2% of the identified ingredient. "Free" means that the composition contains less than 1% of the identified ingredient. A composition containing "no water" or "no acetone" contains about 0% of the identified ingredient. According to certain notable embodiments, the compositions of the present invention are free of acetone and substantially free of water. In certain other embodiments of the invention, the concentration of water may be less than about 20% by weight, such as less than about 15% by weight, less than about 10% by weight in the composition.

In certain embodiments of the invention are essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

The compositions according to the invention can be manufactured by known processes used generally in the cosmetics or dermatological field.

According to certain embodiments, methods of removing nail polish from nails comprising applying a composition for removing nail polish described above to nails onto which nail polish has been previously applied and removing the nail polish from the nails are provided.

According to certain other embodiments, methods of removing nail polish from nails (and optionally moisturizing hands) include the steps of applying a composition for removing nail polish described above to the hands as well as to the nails onto which nail polish has been previously applied; and removing the nail polish from the nails. The composition may also be rinsed from the hands and nails such as with water. In certain embodiments, compositions of the present invention may be advantageously used without an absorbent pad (otherwise commonly used to remove nail polish from the nails).

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I—Stain Prevention Testing

An experiment was conducted to assess cuticle staining from nail polish that was removed with compositions including ethanol, propylene carbonate, glycerin, an acrylic thickener, as well having sucrose, perlite and an organic shell powder suspended therein. The compositions were free of acetone and substantially free of water. Two coats of nail polish (Essie Russian Roulette, L'Oreal of Paris, France) were applied to the finger nails of various individuals. A comparative example (Comparative Example 1) with 4.9% glycerin, a ratio of glycerin to propylene carbonate of about 1:8, and 20% of abrasive was compared with a similar inventive example having a higher ratio of glycerin to propylene carbonate of about 1.15 (Inventive Example 1). It was also compared to another inventive example also having a higher ratio of glycerin to propylene carbonate of about 1.15, but having only 15% abrasive. For each of the compositions to be tested, nail polish on two separate individuals' hands were evaluated. The inventive examples showed no cuticle staining after removal, whereas the comparative composition showed significant staining of the cuticles.

Example II—Stain Prevention Testing #2 (In-Vitro)

Neoprene was chosen as a proxy for keratin/human cuticle material. Neoprene substrates were obtained from cuts of NeoTouch™ Neoprene gloves (5 mil thick, powder free). The green colored gloves were cut open and the surrounding of the glove surface was taped with double sided tape to a black drawdown card. NeoTouch™ gloves are available from Ansell of Iselin, N.J. Five test compositions were prepared with varying amounts of glycerin. The test compositions included ethanol, propylene carbonate, glycerin, an acrylic thickener, as well having sucrose suspended therein. The compositions were free of acetone and substantially free of water. To each of the test compositions, enough nail polish (Essie Russian Roulette, L'Oreal of Paris, France) was added to create a 3.3% solution of nail polish therein. A small drop of the test composition having the nail polish dissolved therein was applied to the neoprene substrate. After five minutes the drop was removed with a cotton pad saturated in deionized water. The remaining stain was visually assessed for intensity and with a colorimeter (Datacolor 600™ from Datacolor Spectrum of Lawrenceville, N.J.). The ratio by weight of glycerin to propylene carbonate (which increases from Example A to Example E) as well as the corresponding test results are shown in Table 1, below.

TABLE 1

| Reference | Ratio by weight of glycerin to propylene carbonate | Staining results |
| --- | --- | --- |
| Example A | 1:7.7 | Continuous staining of surface, slightly darker at rim. |
| Example B | 1:3.6 | Slight staining at rim. Very slight staining toward edges. |
| Example C | 1:2.2 | Slight staining at rim. No staining elsewhere. |
| Example D | 1:1.5 | Slight staining at rim. No staining elsewhere. |
| Example E | 1:1.26 | Slight staining at rim. No staining elsewhere. |

The results above indicate when tested in vitro, we also see that for compositions including ethanol, propylene carbonate and glycerin; when the weight ratio of glycerin to propylene carbonate increases, resistance to cuticle staining surprisingly improves.

Example III—Phase Stability

Thirty-four mixtures of ethanol, glycerin, and propylene carbonate were prepared by combining the ingredients in the relative concentrations by weight listed below. The mixtures were evaluated after one hour by visually assessing the co-miscibility of the mixtures, looking for haze upon shaking the ingredients together as an indication of instability.

| EXAMPLE | Propylene Carbonate | Ethanol | Glycerin | Miscible (M) or Immiscible (I) |
| --- | --- | --- | --- | --- |
| 1 | 32.5 | 30.0 | 37.5 | M |
| 2 | 62.25 | 20.0 | 18.75 | M |
| 3 | 3.75 | 40.0 | 56.25 | M |
| 4 | 60.0 | 40.0 | 0 | M |
| 5 | 5.0 | 20.0 | 75.0 | I |
| 6 | 71.25 | 10.0 | 18.75 | I |
| 7 | 33.75 | 10.0 | 56.25 | I |
| 8 | 31.25 | 50.0 | 18.75 | M |
| 9 | 53.9 | 16.1 | 30.0 | I |
| 10 | 57.2 | 16.1 | 26.7 | I |
| 11 | 68.62 | 8.05 | 23.33 | I |
| 12 | 71.95 | 8.05 | 20.0 | I |
| 13 | 73.3 | 0.0 | 26.7 | I |
| 14 | 53.9 | 16.3 | 30.0 | I |
| 15 | 48.85 | 24.15 | 30.0 | M |
| 16 | 52.52 | 24.15 | 23.33 | M |
| 17 | 44.47 | 32.2 | 23.33 | M |
| 18 | 49.2 | 24.2 | 26.6 | M |
| 19 | 56.54 | 20.13 | 23.33 | M |
| 20 | 41.83 | 28.18 | 30.0 | M |
| 21 | 59.88 | 20.13 | 20.0 | M |
| 22 | 47.8 | 32.2 | 20.0 | M |
| 23 | 53.2 | 20.1 | 26.7 | M |
| 24 | 44.5 | 32.2 | 23.3 | M |
| 25 | 5.1 | 0.0 | 94.9 | I |
| 26 | 0.1 | 0.0 | 99.9 | I |
| 27 | 95.0 | 0.0 | 5.0 | I |
| 28 | 4.5 | 11.5 | 84.0 | I |
| 29 | 4.1 | 19.4 | 76.5 | I |
| 30 | 4.1 | 20.1 | 75.8 | M |
| 31 | 91.1 | 4.2 | 4.8 | I |
| 32 | 89.3 | 6.0 | 4.7 | I |
| 33 | 88.8 | 6.5 | 4.7 | M |
| 34 | 0.1 | 0.3 | 99.6 | M |

The results are further displayed in FIG. 1, which is essentially a phase diagram of the three components. Open circles indicate miscible mixtures and closed circles indicate immiscible mixtures. The results indicate that if one desires to maintain high ratios of glycerin to propylene carbonate (to minimize cuticle staining), one is surprisingly restricted to the levels of ethanol that are greater than about 16% by weight of ethanol. The gap in miscibility is not an intuitive result since all three components have relatively similar polarities.

What is claimed is:

1. A composition for removing nail polish comprising a C2-C3 monoalcohol, glycerin, and propylene carbonate, wherein the glycerin and propylene carbonate are present in a glycerin to propylene carbonate ratio by weight of at least 1:3 and the concentration by weight of ethanol is at least about 16%.

2. The composition of claim 1, wherein the glycerin and propylene carbonate are present in a glycerin to propylene carbonate ratio by weight of at least 1:2.2.

3. The composition of claim 1 comprising a multicomponent solution phase and a suspended solid phase suspended in the multicomponent solution phase.

4. The composition of claim 3 wherein the suspended solid phase includes an abrasive.

5. The composition of claim 3, wherein the abrasive is water soluble.

6. The composition of claim 3, wherein the multicomponent solution phase comprises the C2-C3 monoalcohol, the glycerin, and the propylene carbonate and the multicomponent solution phase further comprises one or more additional components.

7. The composition of claim 6, wherein the one or more additional components comprise no more than about 10% by weight of the multicomponent solution phase.

8. The composition of claim 6, wherein the one or more additional ingredients comprise one or more ingredients selected from a group consisting of a polymeric thickening agent, a fragrance, and water.

9. The composition of claim 1 wherein the composition is substantially free of acetone.

10. The composition of claim 1 wherein the composition is substantially free of water.

11. The composition of claim 1 wherein the composition is substantially free of acetone and substantially free of water.

12. The composition of claim 1 wherein the composition has less than about 5% oil.

13. The composition of claim 1 wherein the concentration by weight of ethanol is at least about 20%.

14. The composition of claim 1 wherein the concentration by weight of glycerin is at least about 10%.

15. The composition of claim 1 wherein the concentration by weight of glycerin is at least about 15%.

16. The composition of claim 1 wherein the concentration by weight of glycerin is at least about 20%.

17. The composition of claim 1 wherein the C2-C3 monoalcohol, glycerin, and propylene carbonate, collectively comprise at least about 75% of the composition.

18. A method of removing nail polish from nails and moisturizing the hands of a subject, comprising:
  applying the composition of claim 1 to hands and to nails of a subject onto which the nail polish had been previously applied; and
  removing the nail polish from the nails.

\* \* \* \* \*